US00PP09947P

United States Patent [19]

Jessel, Jr.

[11] Patent Number: Plant 9,947

[45] Date of Patent: Jul. 8, 1997

[54] CARNATION PLANT VARIETY NAMED 'CFPC GOLDSTRIKE'

[75] Inventor: Walter H. Jessel, Jr., Gonzales, Calif.

[73] Assignee: California Florida Plant Co., L.P., Salinas, Calif.

[21] Appl. No.: 626,533

[22] Filed: Apr. 2, 1996

[51] Int. Cl.[6] ..... A01H 5/00

[52] U.S. Cl. ..... Plt./70.4

[58] Field of Search ..... Plt./70.2, 70.4

*Primary Examiner*—Howard J. Locker

*Attorney, Agent, or Firm*—Christie, Parker & Hale, LLP

[57] ABSTRACT

A new variety of carnation plant producing sprays of yellow flowers with a smooth petal edge.

1 Drawing Sheet

SUMMARY OF THE INVENTION

The present invention relates to a new and distinct variety of carnation plant which was originated by me in a controlled breeding program by my crossing as seed parent the variety known as 'Koreno' and as pollen parent, a proprietary, unnamed and unpatented seedling of my creation identified as No. 890213. The varietal denomination of this new carnation is 'CFPC Goldstrike'.

Among the novel combination of characteristics possessed by the new variety which distinguishes it are sprays of yellow flowers with a smooth petal edge, good disease tolerance and relatively short crop time to flower. The new variety exhibits resistance to soil-borne disease such as *Fusarium oxysporum* and *F. graminearum* and root rots such as damping off, water molds and the like. The flowers are medium to large, spray-type and open fully without bursting the calyx and causing splits.

Asexual reproduction by propagation by side shoot cuttings of the new variety as performed in Salinas, Calif., shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Color Chart (R.H.S.C.C.). The terminology used in color description herein refers to plate numbers in the aforementioned color chart. Color designations and color descriptions may deviate from the stated values depending upon varying environmental, seasonal and cultural conditions.

The information provided herein is based on observations of plants grown inside commercial greenhouses at Salinas, Calif. The height of plant and flower and foliage size are established as an average using standard commerical cultural practices. Where terms such as average, normal, ordinary, etc., are used, the characteristics so described are not considered distinguishing.

Name: 'CFPC Goldstrike'.

Classification:

*Botanical.*—Hybrid, *Dianthus caryophyllus.*

*Commerical.*—Carnation, standard disbud type.

Parentage:

*Female parent.*—'Koreno'.

*Male parent.*—Unnamed seedling (No. 890213).

1. Plant:
   - *Height.*—About 42 inches.
   - *Growing habit.*—Hebaceous, upright.
   - *Blooming habit.*—As a spray.
   - *Breaking action.*—Good.
   - *Rooting time.*—About 16 to 18 days.
   - *Mutation prone.*—No.
   - *Disease resistance.*—Excellent.
   - *Temperature tolerance.*—Wide range.
2. Foliage:
   - *Color.*—Upper side: Near 139A. Lower side: Near 136B.
   - *Size.*—About 6¾ to 7 inches long, about ⅜ inches wide, curled.
   - *Quantity.*—Numerous.
   - *Shape.*—Lanceolate.
   - *Texture.*—Smooth.
   - *Ribs.*—Central, Keeled.
   - *Arrangement.*—Bi-lateral along stem.
   - *Stem color.*—Green.
3. Bud:
   - *Shape.*—Ovoid
   - *Color.*—Green.
   - *Length.*—About 1 inch.
   - *Diameter.*—About ¾ inch.
4. Calyx:
   - *Number of sepals.*—About 5.
   - *Length.*—About 1 inch.
   - *Width.*—About ½ inch.
   - *Color.*—Outside — near 141A, base near 141C. Inside - near 148D.
5. Bloom:
   - *Shape.*—Round.
   - *Size.*—Diameter average: About 2⅝ inches. Depth average: About 1¼ inches.
   - *Borne.*—Terminally as a spray.
   - *Color.*—General tonality: Yellow. Upper side: Near 3B. Lower side: Near 3B. Center: Near 3A. Outer petals: Near 3B.
   - *Keeping quality.*—Very good.
   - *Fragrance.*—Slight to none.
6. Petals:
   - *Number.*—About 43.
   - *Outer petals.*—Length: About 2¼ inches. Width: About 1 inch.

*Central petals.*—Length: About 2 inches. Width: About ¾ inch.

*Texture.*—Smooth.

*Form.*—Fan shaped.

*Appearance.*—Shiny.

7. Reproductive organs:

*Stamens.*—0 to 6.

*Anthers.*—About ⅛ inch, if present, beige.

*Filaments.*—About ½ inch, if present, white.

*Pistil.*—Number: About 4. Color: White. Length: About ⅝ inch.

*Stigma.*—Number: About 4. Color: Base white, apex pale yellow, white at maturity.

*Ovary.*—Shape: Conical, ribbed.

*Fertility.*—Female: Very poor. Male: Fair.

I claim:

1. A new and distinct variety of carnation plant substantially as shown and described.

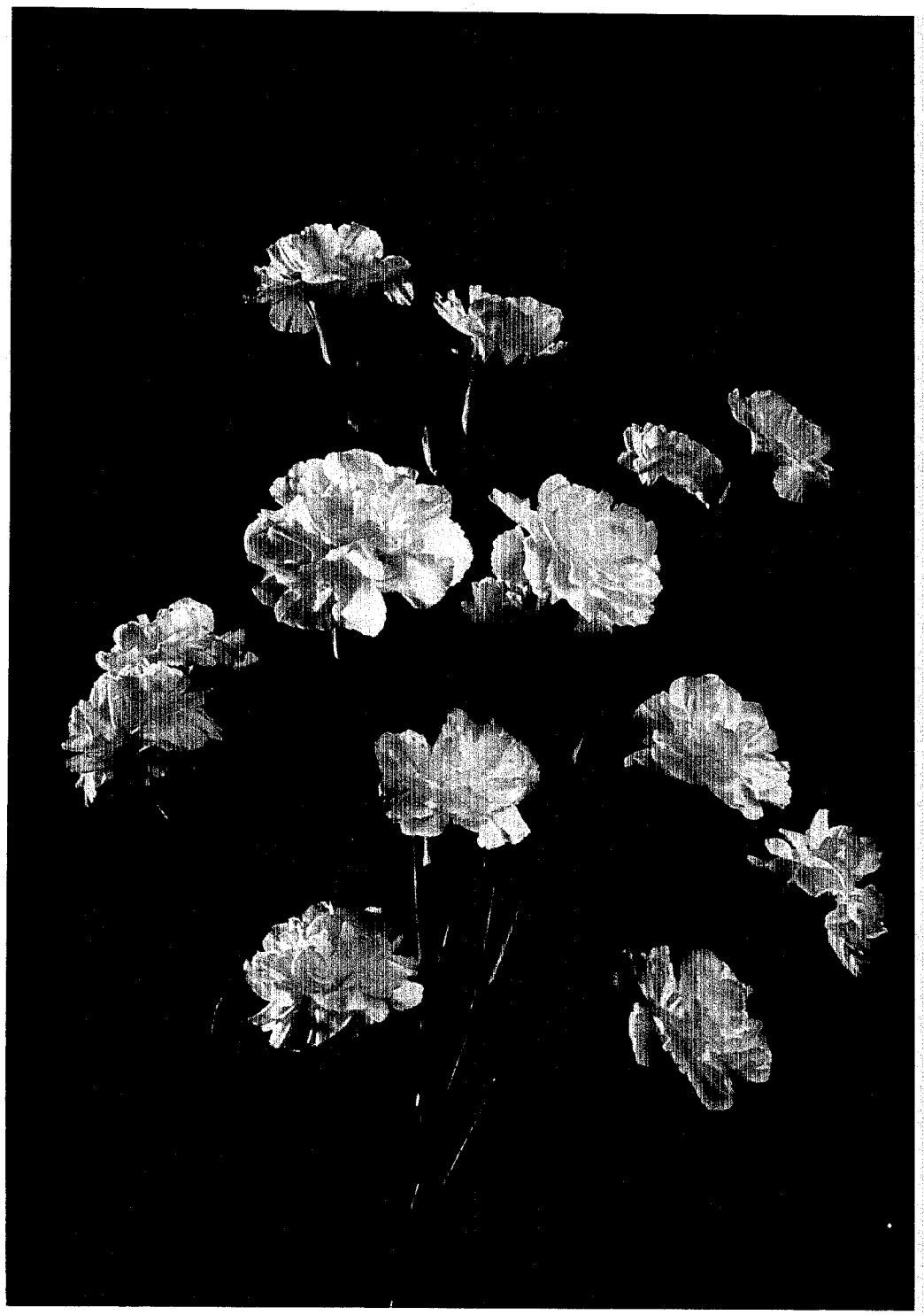

* * * * *